United States Patent
Nowak et al.

(10) Patent No.: US 8,163,513 B2
(45) Date of Patent: Apr. 24, 2012

(54) METHOD FOR DETERMINING THE TOTAL CLOTTING ACTIVITY OF A BLOOD OR PLASMA SAMPLE

(75) Inventors: Götz Nowak, Erfurt (DE); Elke Bucha, Erfurt (DE); Ute Lange, Kahla (DE)

(73) Assignee: JenAffin GmbH, Jena (DE)

( * ) Notice: Subject to any disclaimer, the term of this patent is extended or adjusted under 35 U.S.C. 154(b) by 1160 days.

(21) Appl. No.: 11/884,988

(22) PCT Filed: Feb. 17, 2006

(86) PCT No.: PCT/EP2006/001492
§ 371 (c)(1),
(2), (4) Date: Dec. 11, 2007

(87) PCT Pub. No.: WO2006/089697
PCT Pub. Date: Aug. 31, 2006

(65) Prior Publication Data
US 2008/0138843 A1 Jun. 12, 2008

(30) Foreign Application Priority Data
Feb. 22, 2005 (DE) .......................... 10 2005 008 066

(51) Int. Cl.
*C12Q 1/56* (2006.01)
(52) U.S. Cl. ............................................. 435/13; 435/2
(58) Field of Classification Search .............. 435/2, 13
See application file for complete search history.

(56) References Cited

U.S. PATENT DOCUMENTS

| 6,051,390 | A | 4/2000 | Nowak et al. | |
|---|---|---|---|---|
| 6,207,419 | B1 * | 3/2001 | Church et al. | 435/69.7 |
| 6,743,596 | B1 | 6/2004 | Fischer et al. | |
| 7,172,878 | B1 | 2/2007 | Nowak et al. | |
| 2004/0043428 | A1 | 3/2004 | Adema | |

FOREIGN PATENT DOCUMENTS

| EP | 0420332 | 4/1991 |
|---|---|---|
| EP | 1367135 | 12/2003 |
| WO | WO-96/21740 | 7/1996 |
| WO | WO-00/46602 | 8/2000 |
| WO | WO-00/52199 | 9/2000 |
| WO | WO-03/093831 | 11/2003 |

OTHER PUBLICATIONS

Stone et al. 1986. Kinetics of the Inhibition of Thrombin by Hirudin. Biochemistry, vol. 25, pp. 4622-4628.*
Al Dieri et al. 2002. The Thrombogram in Rare Inherited Coagulation Disorder: Its Relation to Clinical Bleeding. Thromb. Haemost, vol. 88, pp. 576-582.*
Nowak et al. 1996. Quantitative Determination of Hirudin in Blood and Body Fluids. Seminars in Thrombosis and Hemostasis, vol. 22, Issue 02, pp. 197-202.*
Steinmetzer et al., Eur. J. Biochem., 265:598-605 (1999).
Lange et al., Pathophysiology of Haemostasis and Thrombosis, 33:184-191 (Apr. 2003).
F. Markwardt et al. "Die quantitative Bestimrnung des Prothrombins durch Titration mit Hirudin", Arch. exper. Path. u. Pharmakol, vol. 232 pp. 487-498 (1958).
Written Opinion of the International Searching Authority—PCT/EP2006/001492.

* cited by examiner

*Primary Examiner* — Jon P Weber
*Assistant Examiner* — Kailash C Srivastava
(74) *Attorney, Agent, or Firm* — Peter F. Corless; Christine C. O'Day; Edwards Wildman Palmer LLP

(57) ABSTRACT

The invention relates to a method for determining the total clotting activity of a blood or plasma sample, characterized in that a highly specific, reversible thrombin inhibitor is added to a blood or plasma sample in a defined amount, the clotting of the blood or plasma sample is induced and, after a defined period of time, the consumed amount of the added thrombin inhibitor is determined in a per se known manner, as well as to a kit for obtaining information about the state of coagulation of a blood sample.

6 Claims, 1 Drawing Sheet

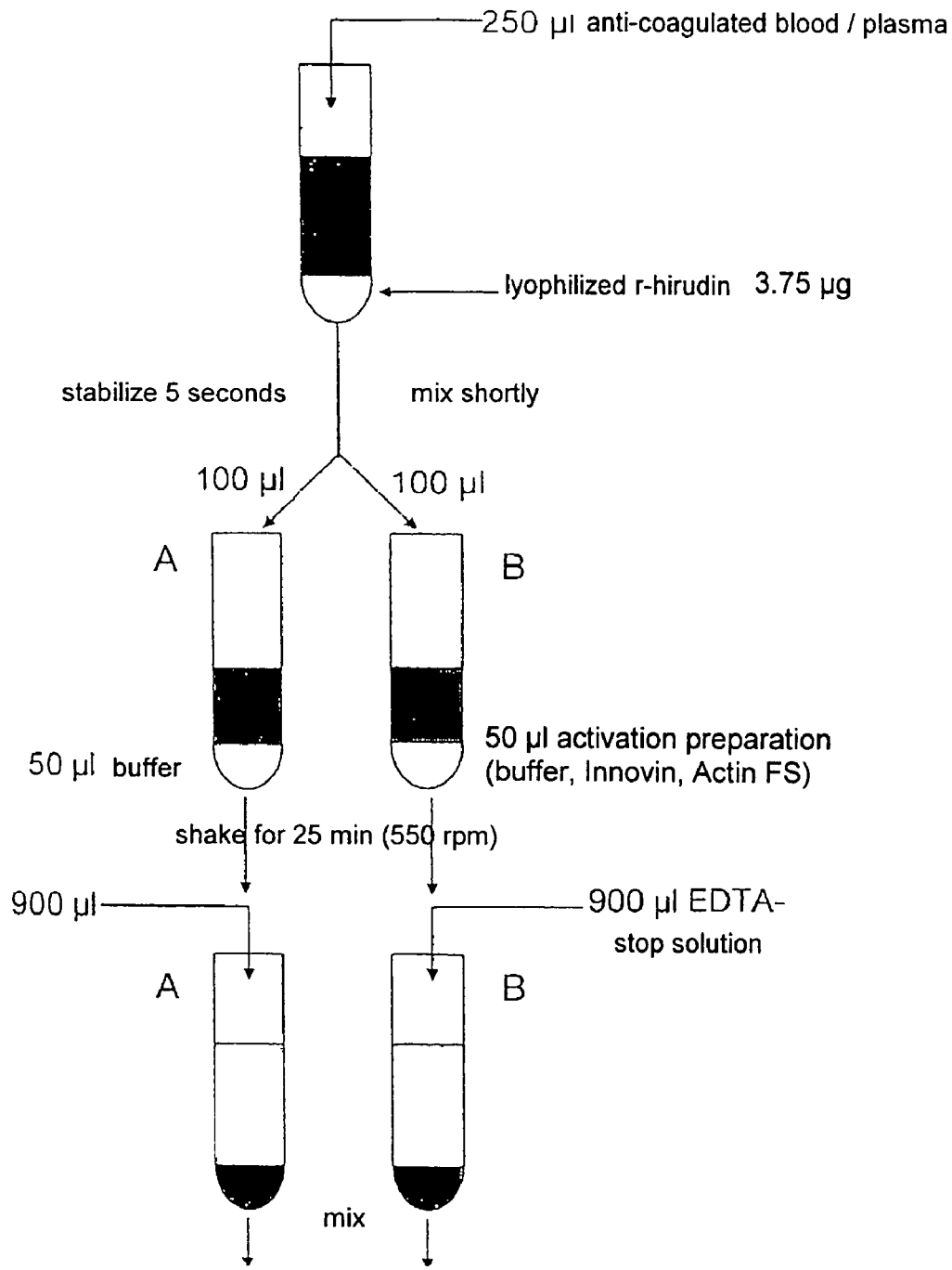

METHOD FOR DETERMINING THE TOTAL CLOTTING ACTIVITY OF A BLOOD OR PLASMA SAMPLE

The present application is a 371 national stage application of PCT/EP2006/001492, filed on Feb. 17, 2006, which claims the prior benefit of German Application No. 10 2005 008 066.9, filed on Feb. 22, 2005.

The invention relates to a method for determining the total clotting activity of a blood or plasma sample. The invention further relates to a kit for performing this method as well as the kit for use in a method for obtaining information about a patient's state of coagulation.

Blood clotting in a human or animal organism is a complex process proceeding in phases, which is triggered by pathological and physiological processes and, in vivo, serves hemostasis. During blood clotting, the soluble fibrinogen which is present in the plasma is converted into the fibrous-gelatinous clotting substance, the fibrin, in a multi-step process (coagulation cascade) involving at least 15 different blood clotting factors, each of which, when being activated, activates the next inactive precursor, respectively.

The serine protease thrombin is the most important enzyme during the activation of the plasmatic coagulation system, in which serine proteases (FXI, FIX, FX) are activated quasi solid-phase-like by activation complexes, generated in several partial steps, composed of precursors of serine proteases, which are fixed to negative charged phospholipids via particular binding structures (γ-carboxyl groups) by means of mediation of calcium ions and co-factors (FVa, FVIIIa). The last product of the complex activation of coagulation, the enzyme thrombin, as the only protease leaves its activation complex and is, thus, available in free form in the blood circulation. There, it meets very different thrombin substrates that both relate to the clotting protein fibrinogen and to cells. Because of this, thrombin has a bridging function between plasmatic coagulation and the cellular elements, particularly the blood platelets, for which thrombin resembles the strongest aggregation-triggering factor. On the phospholipid surface of aggregated platelets, large amounts of activation complexes are located as well, which can then generate thrombin. The global coagulation state of a patient can be read off the maximally possible amount of thrombin in blood and plasma. This so-called thrombin generation potential allows hints as to a hypercoagulability of the blood (thrombophilia), but may also give notice of a hypofunction of thrombin formation (hemophilia, bleeding tendency).

In the prior art, methods for measuring the generation of thrombin in plasma are known. This is generally done by means of global coagulation tests such as aPTT, prothrombin time, Quick's value, reptilase time, batroxobin time, etc. With such tests, however, only a section of the activation of coagulation is covered. In principle, in doing so, in vitro, predominantly in "plasma asservates" ("Plasmaasservaten") of patients, a defined amount of a coagulation inducer is added. That way, a certain amount of α-thrombin activity is activated, which suffices to measure the onset of clotting over time via a recognition system, normally the fibrinogen present in the sample. At this, only 5-8 NIH units thrombin are principally activated per ml of the clotting preparation.

A method for measuring the thrombin generation in plasma is the method according to Hemker et al. (EP 0 420 332). With this method of Hemker, which, in practice, is employed in several modifications, the generation of thrombin is monitored after induction of coagulation while measuring continuously by means of a chromogenic substrate (WO 0052199, WO 03093831, WO 09621740). In doing so, the chromogenic substrate cleavage is added up as an area integral in short time intervals. The rate of the chromogenic substrate cleavage as well as the chromogenic substrate cleavage over time are used as a measure for thrombin generation. With this method, influences of anticoagulant pharmaceuticals as well as clotting disorders can be made measurable by the simultaneous generation of thrombin. The disadvantage of this method is, however, that due to the measuring principle by means of chromogenic and fluorogenic substrates, respectively, and photometric methods, one can only work in translucent materials (plasma or plasma that is rich in platelets). At the same time, a further disadvantage lies in the fact that the plasmas must strongly be diluted for the measurement, which falsifies the contributions of the naturally present inhibitors. Furthermore, in this kind of experimental setups, due to the permanent induction of clotting, an unphysiological enrichment of thrombin occurs so that a unphysiological self-limitation of the action then occurs by means of the slowly reacting inhibitors that are present in the blood (e.g.: $\alpha_2$-macroglobulin). In in vivo-situations, these large amounts of free thrombin are not available since, in undiluted blood, a large number of thrombin substrates (fibrinogen, factors V, VIII and XI, prothrombin), but also anti-thrombins (anti-thrombin II, heparin-cofactor II, amongst others) are present which, depending on the available amount of thrombin, effectively block the same. Furthermore, in this prior art method, only the dynamic activation of thrombin is measured, however, no measurement of an endpoint of the coagulation activity is existent. Thus, there exists a need for a further reliable method for measuring the maximal activatability of thrombin, that is, an endpoint measurement of the coagulation activity.

Therefore, the invention is based on the object to provide a method for measuring the maximal activatability of thrombin in blood or plasma. The method according to the invention shall be independent of variable external influences such as reaction temperature or reaction time, and, with sufficient certainty, shall allow thrombin activation to proceed to the endpoint. Moreover, the method shall also be workable in full blood and with almost undiluted blood samples. Furthermore, the method shall be easily employed and shall allow reliable information about the coagulation state of a blood sample.

Surprisingly, it was now found that this object is solved in that a highly specific, reversible thrombin inhibitor is provided in a certain amount in the blood sample and then, after induction of coagulation, the consumed amount of the added thrombin inhibitor is determined.

The invention, thus, relates to a method for determining the total clotting activity of a blood or plasma sample, which is characterized in that a highly specific, reversible thrombin inhibitor is added to the blood or plasma sample in a defined amount, coagulation is then induced, and the consumed amount of the added thrombin inhibitor is determined in a per se known manner. Furthermore, the invention relates to a kit for performing the method for determining the total clotting activity as well as the kit for use in a method for obtaining information or statements, respectively, about the coagulation state of a patient.

It was found that the maximally possible generation of thrombin is quantifiable as a total quantity in undiluted anti-coagulated blood and/or plasma by means of the method according to the invention. The highly specific, reversible thrombin inhibitor must be provided in a relatively high concentration so that it is on a competitive basis with the thrombin substrates and thrombin receptors that have a high affinity or are present in relatively high concentration, respectively. The providing of 10 to 30 μg highly specific thrombin inhibitor per ml blood or plasma, as a rule, is sufficient. The exact ratio of inhibitor to blood can, however, easily be determined experimentally by means of simple routine experiments.

It is substantial that the highly specific, reversible thrombin inhibitor is an inhibitor, the affinity of which is both directed against the active site of thrombin and additionally against the important recognition structure of the "anion binding exosite 1" (ABE 1). Furthermore, the highly specific thrombin inhibitor must be of no influence for other serine proteases of the prephase activation or main phase activation participating at the coagulation system (Factor VIIa, IXa, Xa, XIa). Such inhibitors are known in the prior art. Examples for such thrombin inhibitors are hirudin, dipetalogastin I and II, thrombin-specific serine protease inhibitors from *Dipetalogaster maximus*, a tropical kissing bug, as well as rhodniin from *Rhodnius prolixus* (kissing bug) and chimeras derived therefrom such as dipetarudin, an inhibitor variant of parts of dipetalogastin and hirudin with similarly high affinity and the same binding specificity and binding features as hirudin. Also bifunctional slow tight binding-inhibitors, such as for example were described in European Journal Biochemistry 265, 598-605, 1999, are suitable according to the invention. Furthermore, also recombinant inhibitors that correspond to the natural inhibitors may be used. Also variants and modifications of the naturally occurring inhibitors may be used as long as the inhibitors posses the features referred to above.

Advantageously, the consumption of the inhibitor provided should very precisely be measurable. In principle, the direct thrombin inhibitors referred to above, particularly inhibitors with tight binding-quality may be determined very precisely with the Ecarin Clotting Time or, in derivation thereof, with the Ecarin Chromogenic Assay (WO 0046602) and may be precisely determined linearly over a wide range. The preferably used thrombin inhibitor is hirudin. Preferably, hirudin is used in an amount of 15 µg/ml blood/plasma.

The blood sample/plasma sample to be examined may be used diluted or undiluted. The blood sample and plasma sample, respectively, is obtained in a per se known manner. Usually, blood samples are obtained in commercially available complete setups. For the method according to the invention, preferably, Sarstedt-Monovettes® 2.7 ml containing 0.3 ml Natrium citricum are used, wherein the blood is obtained via vein puncture of the V. cubitalis. The citrate blood is divided in 2 aliquot halves and 1 sample is then subsequently treated at 3800 rpm for 10 min in a laboratory centrifuge. The supernatant platelet-free plasma is taken off by means of a pipette and than used according to the instructions. It is advantageous when the examination of the citrate blood and citrate plasma is carried out within 2-3 hrs after blood withdrawal. On the other hand or plasma may be stored in the fridge for up to 24 hrs.

In the method according to the invention, a defined amount of thrombin inhibitor in a blood or plasma sample is provided, whereupon in this sample, the clotting is maximally induced by means of intrinsic and/or extrinsic activators and optimal calcium ion concentration. All of the induced clotting potential that can be generated via the extrinsic and/or intrinsic plasmatic clotting way ultimately converts the final serine protease thrombin from the inactive precursor prothrombin. The thrombin generated in the prothrombinase complex and released therefrom is instantly scavenged from the highly specific inhibitor and is inactivated. After a defined period of activation, the activation process is stopped via EDTA. Thereafter, the not-consumed free inhibitor in the sample can be measured by means of a precise efficient determination method. The more thrombin was generated, the larger is the use of the inhibitor in the sample. That way, it is possible to very precisely record the maximal thrombin activation potential of a blood or plasma sample. The inhibitor provided exclusively binds to the permanently activated thrombin, that is to say only the end-product of the coagulation, and in no way influences the events of clotting that occur before that. It is known that the co-enzymes FVa, FVIIa which are activated during the normal clotting events by thrombin, are also activated by the FXa so that the real physiological or pathological events of clotting are reproduced in the method according to the invention.

In the method according to the invention, both of the activation pathways of thrombin known so far, the so-called extrinsic and the intrinsic pathway, are commonly accounted for. An isolated activation of the extrinsic or intrinsic pathway is possible, but is only of significance in the cells, for which there are hints as to an isolated factor deficiency (e.g. by inherited clotting diseases). Other than that, the test is a "global test" for the decision "clotting-sick" or "clotting-healthy". Accordingly, normal values of the method according to the invention exist in blood as well as in plasma. Values diverging therefrom in individual patients provide indications as to a clotting disease. In this respect, it was surprisingly found that, for this, an optimal mixing ratio of the two activator substances must be employed in an optimal activation recipe. Only in doing so, the maximally possible generation ability of thrombin can be measured. Here, in principle, known substances for coagulation induction that can be obtained on the market may be used. Extrinsic activators are usually tissue factors that are produced from a great variety of cell/organ components of animals and of humans. So-called "thromboplastins" or "thrombokinases" are produced from rabbit brain, from lung or liver and, as a rule, can poorly be standardized. It has, therefore, proven advantageous to employ a recombinant product the batches of which do not show major fluctuations of activity. The corresponding is true for the intrinsic activators. Here, both animal and also plant phospholipids are usable, which then additionally contain starters such as ellagic acid as well. Corresponding products are obtainable on the market and are well known to a person skilled in the art. According to the invention it was detected that a combination of the products Innovin and Actin FS (both products of the Dade Behring company) in an optimal manner account for the two activation pathways of the thrombin. The Innovin is a recombinant tissue factor preparation and aims at the exogenic activation pathway. The Actin FS required for the endogenic activation pathway is a so-called activated PTT-reagent, in which both phospholipids and ellagic acid account for the required endogenous activation of coagulation. The assay should also contain a certain optimal amount of calcium ions so that the blood, which was originally anti-coagulated with citrate, is neutralized again and that the clotting factors, which in vivo require the blood's own calcium for their activation, are present under optimal ionic conditions. Furthermore, albumin (preferably bovine albumin) should be present in the assay, which serves the better homogenization of the lipid-like substances, particularly of the endogenic activation pathway. The trivial denomination THROGA (thrombin generation assay) was chosen for the method of the invention.

Hence, the invention also relates to a kit for determining the total clotting activity of a blood sample. This kit comprises the thrombin inhibitor, factors for the extrinsic and intrinsic activation of the thrombin as well as suitable auxiliary reagents. The kit is provided in packaging units that per se are known and that can be produced in a conventional way.

With the method according to the invention and with the kit according to the invention, respectively, the maximally activatable amount of thrombin of a blood or plasma sample can be measured specifically and reliably. Besides, also a basal amount of thrombin in the blood can be measured with this method. In the plasma, a constant small amount of thrombin can always be found. In blood, however, different, both reduced and elevated concentrations of thrombin can be detected ("blind thrombin").

The method of the invention, therefore, provides information about a normal, supernormal or subnormal coagulability of the blood (thrombophilia or hemophilia, respectively, bleeding tendency). Furthermore, a progression control of a therapy with oral anti-coagulants of the cumarin or dicumarol type can be measured with the method of the invention. Compared to the Quick's value that, up to now, was used for this, the method according to the invention (the THROGA-method) has the advantage that oral anti-coagulants can be recorded in their clotting inhibitory potency in full blood. Hence, by means of the method, a patient's bleeding tendency can be recognized at an early stage. In studies, good measuring results could be obtained for the patients that are treated with oral anti-coagulants. Since in oral anti-coagulation therapy, the precursors of the important serine proteases of the coagulation system are present in inactive form, particularly the precursor of the key enzyme thrombin, the prothrombin, it is possible to directly determine the still present clotting potential of such patients and, by recording the generation of thrombin in the blood, to also obtain information as to whether a bleeding tendency exists. Furthermore, by means of the method of the invention, also a long term monitoring of a therapy with other clotting inhibiting pharmaceuticals can be carried out. Experiments showed that patients that are treated with direct anti-thrombin substances such as refludan or melagatran or argatroban may be monitored in their thrombophilic state. Hence, the method of the invention is an "acute method" or "instant method", respectively, ("Akutverfahren") which allows immediate statements as to a patient's complex state of coagulation. With the method of the invention, irregularities in the state of coagulation of the blood can immediately be recognized which allows the quick commencing of corresponding therapeutic steps.

FIG. 1 shows the method of the invention at a glance.

The invention is more closely explained by means of the following examples.

EXAMPLE 1

General Instructions for Performing the Test

For maximal generation of thrombin, a small amount of anti-coagulant blood or plasma is used. For this, citrate, but also every other anti-coagulant may be used. 0.1 ml citrate blood or citrate plasma each are put into a reference tube (NaCl) and an activator tube (tissue factor+mixture of ellagic acid and phospholipids) in which a defined amount of hirudin is present. After closing the reaction vessels, the two containers are mixed in a mini shaker at 550 rpm at room temperature for 25 minutes. The activation of coagulation is subsequently terminated with a stop solution containing EDTA and the remaining not-consumed free hirudin is determined with a precise detection method. For the exact measurement of the hirudin content in the reaction vessels, a commercial available chromogenic hirudin determination method via chromogenic substrate (ECA, Ecarin Chromogenic Assay, WO 0046602) is employed.

EXAMPLE 2

Example of a THROGA-Kit

In the following, an exemplary composition of a THROGA-kit is given:
25× activator tube with lyophilized reagent, identification mark: red label
25× reference tube with lyophilized reagent
1× reference tube with lyophilized reagent for the reference curve, identification mark: closure with red dot
1× 10-fold concentrated stop reagent, 6 ml
2× THROGA-control, lyophilized, for 1.5 ml
2× ECA-prothrombin buffer, lyophilized, for 6 ml
1× ECA-H-substrate, ready-for-use solution, 3 ml
2× ECA-ecarin reagent, lyophilized, for 3 ml.
ECA-prothrombin buffer, ECA-H-substrate, ECA-ecarin reagent: 7 days of use (tested by daily tempering at 37° C. for 3 hrs, storage between the measurements at 2-8° C.)
ECA-prothrombin buffer, ECA-H-substrate, ECA-ecarin reagent, stored in portions and closed at 2-8° C.: 28 days While keeping the reagents at 37° C. in the measuring device, the vials, for protection against evaporation, need to be closed after each withdrawal of reagents. After terminating the operations, the reagents must be stored in a closed state at 2-8° C.

EXAMPLE 3

Conducting the Determination of the Maximal Thrombin Generation in Citrate Blood and/or Plasma Preparation of the Reagents The preset shaker must be turned on at least 30 minutes before the sample tubes are put in. The 10-fold concentrated stop reagent, depending on the respective required amount, needs to be diluted 1:10 with distilled water. The ECA-H-substrate is ready to use. ECA-ecarin reagent, ECA-prothrombin buffer and THROGA-control are dissolved with the amount of distilled water that is denoted on the label and are mixed well but carefully by turning over head. The reagents and the control must be reconstituted at room temperature for 45 min. At least 1× during and after this reconstitution time, the reagents are carefully mixed by turning over head.

Materials and Devices that are Required but Not Contained
    manual clotting measuring device with option for measuring chromogenic reactions Coatron M2 adapted to ECA-H, including consumables and instruction manual (information as to supply at HaemoSys GmbH)
    preset shaker (about 500 rpm)
    stop watch
    deionized or distilled water
    suitable calibrated pipettes with tips
    materials for taking blood samples Specimen/Examination Material
    citrate plasma of citrate blood, centrifuge as soon as possible for at least 10 min at 1500×g and separate plasma.
    carefully mix citrate blood with a ratio of 1 part sodium citrate solution (0.11 mol/l) with 9 parts of venous blood while avoiding formation of foam
    stability of the sample at 15-25° C.: 4 hrs Methodology Thrombin Generation For one determination, 100 μl citrate blood or citrate plasma, respectively, are put into one activator tube and one reference tube each. In order to avoid evaporation, the tubes should be closed after dissolving ("Lösen"). Subsequently, the tubes are put into a shaker for 30-60 minutes. In order to terminate the reaction after shaking, 1000 μl stop reagent are added into each tube and carefully mixed with the pipette.

| reference tube | activator tube |
|---|---|
| 100 μl plasma | 100 μl plasma |
| | 30 min shaking |
| 1000 μl stop reagent | 1000 μl stop reagent |

Determination of the Anti-Thrombin Units (ATU) Via ECA-H

In both THROGA-samples (reference tube and activator tube) the anti-thrombin units (ATU) are now determined via ECA-H.

ECA-H can be used with a multitude of automatic and manual coagulometers which are equipped with an option for optical measurement.

Test Procedure of the Method by Using the Clotting Measuring Device Coatron M2 Adapted to ECA-H The instruction manual of Coatron M2 is to be observed. Upon determining the THROGA in blood samples, the option "auto start" must be inactivated in the device.

The measuring device is pre-warmed to 37° C. The cuvettes are pre-warmed in the cuvette block of the measuring device. ECA-prothrombin buffer, ECA-ecarin reagent and, if possible, the ECA-H-substrate are pre-warmed in the device for at least 15 min.

For avoiding evaporation, the reagents should be closed or covered during the measurement.

Detailed information for performing the test at the Coatron M2 can be taken from the annex of the instruction manual (application ECA-H).

Reagents and THROGA-sample are pipetted into the cuvettes according to the pipetting scheme.

Pipetting Scheme: ECA-H

| pipet into cuvettes pre-warmed to 37° C. | |
|---|---|
| ECA-prothrombin buffer | 100 μl |
| THROGA-sample | 25 μl |
| ECA-H-substrate | 25 μl |
| mix, 1 min incubation at 37° C. | |
| ECA-ecarin reagent | 50 μl |

In case that the addition of the ECA-ecarin reagent is not carried out with a starter pipette, the measuring of time is automatically started 15 seconds after addition of the reagent.

Evaluation

The measuring result is released as measuring time in seconds and as U (anti-thrombin units, ATU). The evaluation is effected via a referential curve that is stored in the measuring device.

From the ATU determined in reference tube and activator tube, respectively, the thrombin units formed in the plasma or blood sample are calculated with the following formula:

$$ETP = R - A$$

ETP maximal endogenic thrombin potential, thrombin units formed in 1 ml blood or plasma
R anti-thrombin units in the reference tube (ATU/ml blood or plasma)
A anti-thrombin units in the activator tube (ATU/ml blood or plasma)

Generating a Reference Curve

In order to obtain correct results, a reference curve must be generated for every new batch of reagents. For generating the reference curve, 25 μl each of THROGA-standard are employed instead of the THROGA-sample. A 4-point-measurement is performed:

Preparation of the THROGA-Standard Dilutions:

| THROGA-standard (concentration in anti-thrombin units/ml plasma) | preparation |
|---|---|
| 224 | reference tube, dissolved in 1100 μl stop reagent |
| 112 | 500 μl standard 225 ATU + 500 μl stop reagent |
| 56 | 500 μl standard 112.5 ATU + 500 μl stop reagent |
| 0 | stop reagent |

It is recommended to perform the measurement of the THROGA-standard as a double-determination. The average values of the ECA-H-reaction times obtained from the measurements are formed and entered into the measuring device together with the respective standard concentrations. In doing so, attention needs to be paid to the fact that U corresponds to the concentration unit ATU/ml blood or plasma. The reference curve is stored in the measuring device.

Detailed information for generating reference curves at the Coatron M2 can be taken from the annex to the instruction manual of the measuring devices (application ECA-H).

Internal Quality Control

For internal quality control, the prepared THROGA-control is employed instead of blood or plasma in the THROGA.

In case that the control value measured is outside the control range indicated on the label of the THROGA-control, reliable determinations are not warranted. The reagents should be checked and, as the case may be, should be replaced. In case that the control value measured is still outside the control range, the functional capability of the measuring device must be checked.

EXAMPLE 4

Examination of Patients by Means of THROGA:
a) Subjects: I. N., female, 37 years

| | r-hirudin concentration (μg/ml) blood | 1 μg = 15.8 ATU plasma |
|---|---|---|
| Control (A) | 14.9 | 14.6 |
| Activated sample (B) | 9.3 | 7.5 |
| Difference (μg/ml) | 5.6 | 7.1 |
| ATU/ml; TU/ml | 88.5 | 112.2 |

Evaluation: I.N. has a "normal" activation amount of 112.2 in the plasma (N: 122 ± 19 TU/ml)

In the blood of the subject, 88.5 TU/ml generated thrombin have been measured. The normal value is at 78±13 TU/ml. With that, she also lies in the normal range.

b) Patients: C. R., female, 55 years, state after cerebral insult

1. Prior to start of a blood platelet-specific therapy with clopidogrel (7.1.04)

|  | r-hirudin concentration (µg/ml) blood | 1 µg = 15.8 ATU plasma |
|---|---|---|
| Control (A) | 13.2 | 14.2 |
| Activated sample (B) | 6.9 | 6.7 |
| Difference (µg/ml) | 6.3 | 7.5 |
| ATU/ml; TU/ml | 99.5 | 118.5 |

2. After 8 weeks of treatment with clopidogrel, 1.5 tablets daily (112.5 mg), (4.3.04)

|  | r-hirudin concentration (µg/ml) blood | 1 µg = 15.8 ATU plasma |
|---|---|---|
| Control (A) | 14.1 | 14.3 |
| Activated sample (B) | 8.9 | 6.9 |
| Difference (µg/ml) | 5.2 | 7.4 |
| ATU/ml; TU/ml | 82.2 | 116.9 |

Evaluation: Upon initial examination, patient C. R. had a pathological THROGA-value in the blood of 99.5 (norm: 78±13 TU/ml) which has normalized after 8 weeks of platelet-specific therapy (82.2). In both examinations, the THROGA-plasma values were within the normal range! In all further controls under clopidogrel therapy, the THROGA-values were normal.

c) Patient M. F., male, 64 years, diagnosis: thrombophilia upon gammopathy; patient obtains thrombosis prophylaxis with falithrom (oral anti-coagulant), 12.2.05

Use of the Kit:

|  | Blood (ATU/ml) | Plasma (ATU/ml) |
|---|---|---|
| Control (A) | 265.4 | 257.5 |
| Activated sample (B) | 219.1 | 218.2 |
| Difference (µg/ml) | 46.3 | 39.3 |

Evaluation: With 39.3 TU/ml in the plasma, patient M. F. had 32% of the normal plasma value and is, thus, within a sufficient "therapeutic window". In the blood, with 46.3 TU/ml, still 60% of the normal generable thrombin amount were detected. With that, no bleeding tendency can be observed and this patient is optimally cared for and supplied, respectively.

The invention claimed is:

1. A method for determining the total clotting activity of a blood or plasma sample, the method comprising:
    adding a highly specific, reversible thrombin inhibitor to a blood or plasma sample in a defined amount,
    inducing the clotting of the blood or plasma sample by addition of extrinsic and intrinsic factors; and
    determining the consumed amount of the added thrombin inhibitor.

2. The method of claim 1, wherein the consumed amount of the added thrombin inhibitor is determined after a defined period of time.

3. The method of claim 1, wherein the thrombin inhibitor is directed to the active site in the thrombin and against the "anion binding exosite 1" (ABE 1).

4. The method of claim 1, wherein the thrombin inhibitor is a synthetic, natural or nature-identical inhibitor.

5. The method of claim 1, wherein the thrombin inhibitor is selected from the group consisting of dipetalogastin I, dipetalogastin II, rhodniin and hirudin.

6. The method of claim 1, wherein induction of clotting is generated by a tissue factor and a mixture of ellagic acid and phospholipids.

* * * * *